(12) United States Patent
Banov

(10) Patent No.: US 9,867,775 B2
(45) Date of Patent: *Jan. 16, 2018

(54) TOPICAL PHARMACEUTICAL BASES FOR TREATING INFLAMMATORY DISORDERS

(71) Applicant: Professional Compounding Centers of America (PCCA), Houston, TX (US)

(72) Inventor: Daniel Banov, Sugar Land, TX (US)

(73) Assignee: Professional Compounding Centers of America, Houston, TX (US)

( * ) Notice: Subject to any disclaimer, the term of this patent is extended or adjusted under 35 U.S.C. 154(b) by 134 days.

This patent is subject to a terminal disclaimer.

(21) Appl. No.: 14/830,945

(22) Filed: Aug. 20, 2015

(65) Prior Publication Data

US 2016/0051609 A1 Feb. 25, 2016

Related U.S. Application Data

(60) Provisional application No. 62/039,782, filed on Aug. 20, 2014.

(51) Int. Cl.
| | |
|---|---|
| *A61K 36/00* | (2006.01) |
| *A61K 9/00* | (2006.01) |
| *A61K 36/32* | (2006.01) |
| *A61K 45/06* | (2006.01) |
| *A61K 31/015* | (2006.01) |
| *A61K 36/47* | (2006.01) |

(52) U.S. Cl.
CPC .......... *A61K 9/0014* (2013.01); *A61K 31/015* (2013.01); *A61K 36/32* (2013.01); *A61K 36/47* (2013.01); *A61K 45/06* (2013.01)

(58) Field of Classification Search
None
See application file for complete search history.

(56) References Cited

U.S. PATENT DOCUMENTS

| | | | | |
|---|---|---|---|---|
| 2010/0284943 | A1* | 11/2010 | Frota Corr a | A01N 65/00 424/47 |
| 2012/0202882 | A1* | 8/2012 | Banov | A61K 9/00 514/570 |

* cited by examiner

*Primary Examiner* — Qiuwen Mi
(74) *Attorney, Agent, or Firm* — David G. Woodral; Scott R. Zingerman; Gable Gotwals

(57) ABSTRACT

The present disclosure refers to topical pharmaceutical bases that possess anti-inflammatory properties. Further, these topical pharmaceutical bases are proposed for treating inflammatory disorders, such as swollen tissues within joints and muscles, and the like. The topical pharmaceutical bases include Amazonian oils and resins, such as pracaxi oil and breu-branco resin. The synergistic effect of pracaxi oil combined with breu-branco resin results in a highly effective anti-inflammatory treatment. Suitable active pharmaceutical ingredients (APIs) can be incorporated to the topical pharmaceutical bases to formulate topical pharmaceutical compositions, which improve anti-inflammatory effects. The synergistic effect provided by the combination of pracaxi oil and breu-branco resin enables lower dosage requirements of the associated APIs when topical pharmaceutical compositions are employed for treating inflammatory disorders.

10 Claims, No Drawings

TOPICAL PHARMACEUTICAL BASES FOR TREATING INFLAMMATORY DISORDERS

CROSS-REFERENCE TO RELATED APPLICATIONS

This application claims priority to U.S. Provisional Application Ser. No. 62/039,782, filed Aug. 20, 2014, which is hereby incorporated by reference herein.

BACKGROUND

Field of the Disclosure

The present disclosure relates generally to pharmaceutical compositions, and more particularly, to topical pharmaceutical bases including natural components for treating inflammatory disorders.

Background Information

Inflammation is a process in which the body's white blood cells and different substances (inflammatory mediators) help to protect the organism from infections and foreign pathogens such as bacteria and viruses. However, in some diseases the body's immune system triggers an inflammatory response even when there are no foreign substances to fight off. When inflammation occurs, inflammatory mediators are released into the blood or affected tissues. This release of inflammatory mediators increases the blood flow to the area of injury or infection and results in redness and warmth. Additionally, some of the inflammatory mediators cause a leak of fluid into the tissues, resulting in swelling. This process stimulates nerves and causes pain.

Additionally, the increased blood flow and release of the chemicals attract white blood cells to the sites of inflammation. As a consequence, the increased number of cells and inflammatory substances causes irritation and swelling.

The most common inflammation sites in the body are the joints and the muscles. Many patients suffer from pain in the back, knee, hip, and fingers. Despite common beliefs, muscle and joint pain is not an inevitable sign of aging, nor are they usually a sign of a condition such as arthritis. Instead, muscle and joint pain is most often a sign of chronic inflammation or hormonal imbalance. Additionally, muscle inflammation is also caused by an allergic reaction, exposure to a toxic substance or medicine, another disease such as cancer or rheumatic conditions, a virus or other infectious agents.

Traditional muscle and joint inflammation treatments include medication, physical therapy, exercise, heat therapy (including microwave and ultrasound), orthotics, and assistive devices, among others.

Commonly employed medications for anti-inflammatory treatments include non-steroidal anti-inflammatory drugs (NSAID). These formulations may cause severe side-effects (e.g., gastrointestinal bleeding, liver damage, and increased risk of heart attack, stroke, and other cardiovascular events). Therefore, there is a need for improved anti-inflammatory treatments that does not include aforementioned side-effects.

SUMMARY

The present disclosure refers to topical pharmaceutical bases that possess anti-inflammatory properties. Further, these topical pharmaceutical bases are proposed for treating inflammatory disorders. In some embodiments, inflammatory disorders include swollen tissues within joints and muscles, and the like.

In some embodiments, the topical pharmaceutical bases include natural components from the Amazon forest. In these embodiments, the topical pharmaceutical bases include pracaxi oil and breu-branco resin. Further to these embodiments, aforementioned natural components exhibit anti-inflammatory and analgesic properties.

In an example, the topical pharmaceutical bases include: pracaxi oil in a concentration from about 1% w/w to 100% w/w, preferably from about 10% to 20% w/w; and breu-branco in a concentration from about 5% w/w to 50% w/w, preferably about 10% w/w.

In other embodiments, the topical pharmaceutical bases include one or more natural components, such as, for example buriti oil, copaiba balsam, bacaba oil, acai oil, ojon oil, andiroba oil, murumuru butter, and/or tucuma oil, among others. In these embodiments, aforementioned natural components improve skin penetration as well as healing properties. Further to these embodiments, the concentration of each natural component within topical pharmaceutical bases is from about 1% w/w to 20% w/w, more preferably about 5% w/w.

In some embodiments, the topical pharmaceutical bases are in a dosage form selected from the group consisting of: pharmaceutically acceptable liquids, creams, oils, lotions, ointments, gels, roll-on liquids, skin patches, sprays, and synthetic polymer dressings, among others.

In some embodiments, the topical pharmaceutical bases are directly administered onto the affected area. In these embodiments, suitable applicators are employed to administer the topical pharmaceutical bases. In an example, suitable applicators include a swab, brush, cloth, pad, and sponge, among others.

In some embodiments, when the topical pharmaceutical bases are applied onto the affected area, the topical pharmaceutical bases deliver a therapeutically effective amount of fatty acids including behenic acid, triterpenes $\alpha$, $\beta$ amyrins, and other aforementioned components, which help in the treatment of swollen tissues. In these embodiments, the synergistic effect of pracaxi oil combined with breu-branco resin within the topical pharmaceutical bases results in a highly effective anti-inflammatory topical formulation, especially for swollen tissues within joints and muscles, and the like.

In other embodiments, active pharmaceutical ingredients (APIs) are incorporated into the topical pharmaceutical bases to formulate topical pharmaceutical compositions. In these embodiments, the synergistic effect provided by the combination of pracaxi oil and breu-branco resin enables lower dosage requirements of the associated APIs when topical pharmaceutical compositions are employed for treating inflammatory disorders.

In some embodiments, various additives are included to facilitate the preparation of suitable dosage forms. For example, additives include gelling agents, thickening agents, pH adjusters, preservatives, colors, stabilizing agents, antioxidants, and surfactants, among others.

Numerous other aspects, features, and benefits of the present disclosure may be made apparent from the following detailed description.

DETAILED DESCRIPTION

The present disclosure is here described in detail with reference to embodiments. Other embodiments may be used and/or other changes may be made without departing from the spirit or scope of the present disclosure. The illustrative embodiments described in the detailed description are not meant to be limiting of the subject matter presented herein.

Definitions

As used here, the following terms have the following definitions:

"Active Pharmaceutical Ingredients (APIs)" refer to chemical compounds that induce a desired effect, and include agents that are therapeutically effective, prophylactically effective, or cosmeceutical effective.

"Oil" refers to a vegetable substance that may be clear, odorless, viscous, hydrophobic, liquid or liquefiable at room temperature.

"Patient" refers to warm-blooded animals, such as mammals, for example, humans, who are in need of treatment.

"Resins" refer to a hydrocarbon secretion of many plants, which possesses valuable chemical properties.

"Therapeutically effective amount" refers to the amount of subject compound that will elicit the biological or medical response of a tissue, system, animal or human that is being sought.

"Treating" and "Treatment" refers to reduction in severity and/or frequency of symptoms, elimination of symptoms and/or underlying cause, prevention of the occurrence of symptoms and/or their underlying cause, and improvement or remediation of damage.

DESCRIPTION OF THE DISCLOSURE

The present disclosure refers to topical pharmaceutical bases that possess anti-inflammatory properties. Further, these topical pharmaceutical bases are proposed for treating inflammatory disorders. In some embodiments, inflammatory disorders include swollen tissues within joints and muscles, and the like.

Formulation

In some embodiments, the topical pharmaceutical bases include natural components from the Amazon forest. In these embodiments, the topical pharmaceutical bases include pracaxi oil and breu-branco resin. Further to these embodiments, aforementioned natural components exhibit anti-inflammatory and analgesic properties.

In an example, the topical pharmaceutical bases include: pracaxi oil in a concentration from about 1% w/w to 100% w/w, preferably from about 10% to 20% w/w; and breu-branco in a concentration from about 5% w/w to 50% w/w, preferably about 10% w/w.

Pracaxi Oil

Pracaxi oil is obtained from the seed oil of the *Pentaclethara macroloba* tree, or pracaxi tree. The pracaxi tree is a deciduous tree from the legumes family, growing in altitudes below 600 meters in many parts of northern Brazil, Guyana, Trinidad, and parts of Central America, and may reach between about 8 and about 35 meters in height. Pracaxi trees may sometimes be found in wetlands, and are resistant to water logging.

Pracaxi seeds include from about 45% to 48% fat, about 27% to 28% protein, and about 12% to 14% carbohydrates (see Table 1). Pracaxi seed oil includes the highest known natural concentration of behenic acid (about 20%) in a vegetable fat, more than six times higher than in peanut oil, and also includes about 35% of oleic acid. In some cases, pracaxi seed oil may include greater percentages of the aforementioned behenic acid and oleic acid. The oleic acid and lauric acid, contained within pracaxi oil, are effective vehicles for delivering drugs through the skin.

TABLE 1

General composition of pracaxi oil.

| Components | Composition |
|---|---|
| Fat | 45-48 |
| Protein | 27-28 |
| Carbohydrates | 12-14 |

In an example, the fatty acid composition of the pracaxi oil is illustrated below in Table 2. Compositions vary depending on the region and conditions in which the pracaxi tree grows.

Pracaxi oil has been widely employed within pharmaceutical compositions because of its cosmetic, therapeutic, and medicinal properties. Pracaxi oil is rich in organic acids with antioxidant, antibacterial, antiviral, antiseptic, antifungal, anti-parasitic, and anti-hemorrhagic properties. Because pracaxi oil possesses many of the aforementioned properties, pracaxi oil can be suitable oil for helping in the treatment of swollen tissues, for example, within joints and muscles.

TABLE 2

Fatty acid composition of the pracaxi oil.

| Fatty Acids | Carbon Atoms | Composition % |
|---|---|---|
| Lauric | 12:00 | 1.30 |
| Myristic | 14:00 | 1.21 |
| Palmitic | 16:00 | 2.04 |
| Stearic | 18:00 | 2.14 |
| Oleic | 18:10 | 44.32 |
| Linoleic | 18:20 | 1.96 |
| Linolenic | 18:30 | 2.31 |
| Behenic | 22:00 | 9.67 |
| Lignoceric | 24:00 | 14.81 |

TABLE 3

Specifications of the pracaxi oil.

| Indicators | Reference Value |
|---|---|
| Texture | Solid below 18.5° C., liquid viscous texture above this temperature |
| Color | Translucent yellow, yellowish-white when solid |
| Odor | Almost odorless |
| Melting point | 18.5° C. |
| Refractive index (40° C.) | 1.4690 |
| Iodine value | 65-70 g IZ/100 g |
| Saponification value | 170-180 mg KOH/g |
| Acid value | 3-5 mg KOH/g |
| Peroxide value | 5-10 mEQ/kg |
| Density (25°) | 0.917 g/cm$^3$ |

Pracaxi oil has a high amount of solid matter, not fatty acids, which makes pracaxi oil solidifies in cooler temperatures. The solid matter has gentle moisturizing and high cellular renewal promoting properties. It includes vitamin E, and has essential fatty acids, which makes pracaxi oil suitable for topical pharmaceutical compositions.

Breu-Branco Resin

Breu-branco resin (*Protium heptaphyllum, Burseraceae*) is extracted from an Amazon jungle tree called Almécega.

Almécega is a tree that grows in dry forests and is native to most of Brazil. The Almécega trees give off an aromatic fragrance and have a dark red bark. Additionally, Almécega trees grow from about 10 to 20 meters in height, and from about 50 to 60 centimeters in diameter at the base.

When a cut is made in the trunk of Almécega trees, the breu-branco resin exudes. This resin has a white-green color and a very pleasant fragrant aroma. Additionally, the breu-branco resin hardens when coming in contact with air. In several areas of Brazil, the resin is collected from the trunk of Almécega trees, and then ground manually after it hardens. Typically, breu-branco resin is collected year round, but especially in the summer season. After the resin is collected, the resin is dried in the shade and then stored in sacks made of fibers, such as jute. Cuts on an Almécega tree to extract the resin are first made when the tree is about 8 to 10 years old. To harvest the resin of this species sustainably, it is recommended that each Almécega tree receives only about 2 to about 3 cuts per year.

Additionally, yields vary according to the process of extraction. For example, the process of hydro-distillation yields about 11% resin, whereas steam distillation yields about 2.5% resin. The general composition of the resin of breu-branco is provided in Table 4, while the monoterpene composition within the resin of breu-branco is provided in Table 5.

TABLE 4

Composition of breu-branco resin.

| Ingredients | Composition % |
|---|---|
| Resinic acids | 60-75 |
| Terpenes | 10-15 |
| Various substances/water | 5-10 |

TABLE 5

Composition of breu-branco resin monoterpene.

| Monoterpenes | Composition % |
|---|---|
| α-pyrene | 10.50 |
| Limonene | 16.90 |
| α-phellandrene | 16.70 |
| Terpinoiene | 28.50 |
| Others | 27.40 |

Breu-branco resin is often used in Amazonian regions for treating some physical conditions. Breu-branco resin is aromatic and rich in triterpenes α, β amyrins, which possess analgesic and anti-inflammatory properties. In traditional medicine, the resin of breu-branco is suggested for asthma, bronchitis, coughs, headaches stomach aches, liver disorders, memory loss, concentration, motor coordination, for soothing states of agitation and stress, as an anti-inflammatory and analgesic, for wound healing, and as a stimulating agent, among others. Due to breu-branco resin's aromatic properties, it is widely used in perfumes and toiletries as well as in soap manufacturing.

In other embodiments, the topical pharmaceutical bases include one or more natural components, such as, for example buriti oil, copaiba balsam, bacaba oil, acai oil, ojon oil, andiroba oil, murumuru butter, and/or tucuma oil, among others. In these embodiments, aforementioned natural components improve skin penetration as well as healing properties. Further to these embodiments, the concentration of each natural component within topical pharmaceutical bases is from about 1% w/w to 20% w/w, preferably about 5% w/w.

In further embodiments, active pharmaceutical ingredients (APIs) are incorporated into the topical pharmaceutical bases to formulate topical pharmaceutical compositions. In these embodiments, the topical pharmaceutical compositions are proposed for treating inflammatory disorders, such as swollen tissues within joints and muscles, and the like.

Administration

In some embodiments, the topical pharmaceutical bases are in a dosage form selected from the group consisting of: pharmaceutically acceptable liquids, creams, oils, lotions, ointments, gels, roll-on liquids, skin patches, sprays, and synthetic polymer dressings, among others.

In some embodiments, the topical pharmaceutical bases are directly administered onto the affected area (e.g., swollen joints and muscles). In these embodiments, suitable applicators are employed to administer the topical pharmaceutical bases. In an example, suitable applicators include a swab, brush, cloth, pad, and sponge, among others.

In some embodiments, when the topical pharmaceutical bases are applied onto the affected area, the topical pharmaceutical bases deliver a therapeutically effective amount of fatty acids including behenic acid, triterpenes α, β amyrins, and other aforementioned components, which help in the treatment of swollen tissues. In these embodiments, the synergistic effect of pracaxi oil combined with breu-branco resin within the topical pharmaceutical bases results in a highly effective anti-inflammatory topical formulation, especially for joints and muscles. Further to these embodiments, the synergistic effect provided by the combination of pracaxi oil and breu-branco resin enables lower dosage requirements of the associated APIs when topical pharmaceutical compositions are employed for treating inflammatory disorders.

In some embodiments, various additives are included to facilitate the preparation of suitable dosage forms. For example, additives include gelling agents, thickening agents, pH adjusters, preservatives, colors, stabilizing agents, antioxidants, and surfactants, among others.

While various aspects and embodiments have been disclosed, other aspects and embodiments are contemplated. The various aspects and embodiments disclosed are for purposes of illustration and are not intended to be limiting, with the true scope and spirit being indicated by the following claims.

What is claimed is:

1. A transdermal pharmaceutical composition comprising:
about 1% w/w to about 95% w/w pracaxi oil,
a synergistically effective amount of breu-branco resin, and
a pharmaceutically effective amount of at least one active pharmaceutical ingredient.

2. The transdermal pharmaceutical composition of claim 1, wherein the transdermal pharmaceutical composition comprises about 5% w/w to about 50% w/w breu-branco resin.

3. The transdermal pharmaceutical composition of claim 2, wherein the transdermal pharmaceutical composition comprises about 10% w/w to about 20% w/w pracaxi oil.

4. The transdermal pharmaceutical composition of claim 2, wherein the transdermal pharmaceutical composition comprises about 10% w/w breu-branco resin.

5. The transdermal pharmaceutical composition of claim 3, wherein the transdermal pharmaceutical composition comprises about 10% w/w breu-branco resin.

6. The transdermal pharmaceutical composition of claim 1, wherein the transdermal pharmaceutical composition further comprises at least one natural component selected from the group consisting of buriti oil, copaiba balsam, bacaba oil, acai oil, ojon oil, andiroba oil, murumuru butter, and tucuma oil.

7. The transdermal pharmaceutical composition of claim 1, wherein the transdermal pharmaceutical composition further comprises at least one natural component selected from the group consisting of about 1% w/w to about 20% w/w buriti oil, about 1% w/w to about 20% w/w copaiba balsam, about 1% w/w to about 20% w/w bacaba oil, about 1% w/w to about 20% w/w acai oil, about 1% w/w to about 20% w/w ojon oil, about 1% w/w to about 20% w/w andiroba oil, about 1% w/w to about 20% w/w murumuru butter, and about 1% w/w to about 20% w/w tucuma oil.

8. The transdermal pharmaceutical composition of claim 3, wherein the transdermal pharmaceutical composition further comprises at least one natural component selected from the group consisting of about 1% w/w to about 20% w/w buriti oil, about 1% w/w to about 20% w/w copaiba balsam, about 1% w/w to about 20% w/w bacaba oil, about 1% w/w to about 20% w/w acai oil, about 1% w/w to about 20% w/w ojon oil, about 1% w/w to about 20% w/w andiroba oil, about 1% w/w to about 20% w/w murumuru butter, and about 1% w/w to about 20% w/w tucuma oil.

9. The transdermal pharmaceutical composition of claim 1, wherein the transdermal pharmaceutical composition further comprises at least one natural component selected from the group consisting of about 5% w/w buriti oil, about 5% w/w copaiba balsam, about 5% w/w bacaba oil, about 5% w/w acai oil, about 5% w/w ojon oil, about 5% w/w andiroba oil, about 5% w/w murumuru butter, and about 5% w/w tucuma oil.

10. The transdermal pharmaceutical composition of claim 1, wherein the transdermal pharmaceutical composition is selected from the group consisting of a pharmaceutically acceptable liquid, a cream, an oil, a lotion, an ointment, a gel, a roll-on liquid, a skin patch, a spray, and a synthetic polymer dressing.

* * * * *